United States Patent
Witt et al.

(10) Patent No.: US 7,798,146 B2
(45) Date of Patent: Sep. 21, 2010

(54) ORAL APPLIANCE

(75) Inventors: Erik K. Witt, Murrysville, PA (US); Charles Thomas, Monroeville, PA (US)

(73) Assignee: RIC Investments, LLC, Wilmington, DE (US)

( * ) Notice: Subject to any disclaimer, the term of this patent is extended or adjusted under 35 U.S.C. 154(b) by 1259 days.

(21) Appl. No.: 11/260,554

(22) Filed: Oct. 27, 2005

(65) Prior Publication Data

US 2006/0096600 A1 May 11, 2006

Related U.S. Application Data

(60) Provisional application No. 60/623,331, filed on Oct. 29, 2004, provisional application No. 60/668,625, filed on Apr. 5, 2005.

(51) Int. Cl.
*A61M 11/00* (2006.01)

(52) U.S. Cl. ............... 128/206.29; 128/207.14

(58) Field of Classification Search ............ 128/201.26, 128/201.27, 205.22, 205.25, 206.29, 207.14, 128/205.19, 200.26, 207.15
See application file for complete search history.

(56) References Cited

U.S. PATENT DOCUMENTS

| 4,350,154 | A | 9/1982 | Feldbau | |
|---|---|---|---|---|
| 4,432,728 | A | 2/1984 | Skarky | |
| 5,203,324 | A * | 4/1993 | Kinkade | 128/201.11 |
| 5,537,994 | A | 7/1996 | Thornton | |
| 5,865,170 | A * | 2/1999 | Moles | 128/201.26 |
| 5,884,625 | A | 3/1999 | Hart | |
| 5,950,624 | A | 9/1999 | Hart | |
| 5,957,133 | A | 9/1999 | Hart | |
| 5,970,976 | A | 10/1999 | Zhao | |
| 5,983,892 | A | 11/1999 | Thornton | |
| 6,209,542 | B1 | 4/2001 | Thornton | |
| 6,374,824 | B1 | 4/2002 | Thornton | |
| 6,571,798 | B1 | 6/2003 | Thornton | |
| D479,876 | S | 9/2003 | Gardon et al. | |
| 6,679,257 | B1 | 1/2004 | Robertson et al. | |
| 6,966,319 | B2 * | 11/2005 | Fitton | 128/848 |
| 7,328,698 | B2 * | 2/2008 | Scarberry et al. | 128/200.24 |
| 2001/0047805 | A1 | 12/2001 | Scarberry et al. | |
| 2003/0015198 | A1 | 1/2003 | Heeke et al. | |
| 2003/0089371 | A1 | 5/2003 | Robertson et al. | |
| 2003/0192549 | A1 | 10/2003 | Boussignac | |
| 2004/0050389 | A1 | 3/2004 | Boussignac | |
| 2004/0134490 | A1 | 7/2004 | Robertson et al. | |
| 2004/0134491 | A1 | 7/2004 | Pflueger et al. | |

FOREIGN PATENT DOCUMENTS

| EP | 0 818 213 A2 | 1/1998 |
|---|---|---|
| WO | WO 01/43673 A1 | 6/2001 |

* cited by examiner

*Primary Examiner*—Steven O Douglas

(57) ABSTRACT

An oral appliance is provided for installation within the oral cavity of a user. The oral appliance is configured to be connected to a negative pressure supply to create a negative pressure environment within the oral cavity of a user. The device includes apertures adjacent the user's teeth.

17 Claims, 18 Drawing Sheets

ORAL APPLIANCE

CROSS-REFERENCE TO RELATED APPLICATIONS

This application claims priority under 35 U.S.C. §119(e) from U.S. provisional patent application No. 60/623,331 filed Oct. 29, 2004 and U.S. provisional patent application No. 60/668,625 filed Apr. 5, 2005 the contents of which are incorporated herein by reference.

BACKGROUND OF THE INVENTION

1. Field of the Invention

The present invention pertains to oral appliances, and, in particular, to oral appliances adapted to prevent partial or complete upper airway obstruction.

2. Description of the Related Art

Obstructive sleep apnea or OSA, obstructive sleep hypopnea, and upper airway resistance syndrome (UARS) are among a variety of known disorders characterized by episodes of complete or partial upper airway obstruction during a state of diminished consciousness, such as sleep, anesthetization, or post anesthesia. OSA, hypopnea, and UARS cause intermittent interruption of ventilation during sleep with the consequence of potentially severe oxyhemoglobin desaturation. Typically, those afflicted with OSA, hypopnea, and UARS experience repeated, frequent arousal from sleep in response to the oxygen deprivation. The arousals result in sleep fragmentation and poor sleep continuity.

Consequences of OSA, hypopnea, and UARS may include debilitating daytime sleepiness and cognitive dysfunction, systemic hypertension, cardiac dysrythmias, pulmonary artery hypertension, and congestive heart failure. Other consequences may include a predisposition to myocardial infarction, angina pectoris, stroke, right ventricular dysfunction with cor pulmonale, carbon dioxide retention during wakefulness as well as during sleep, and continuous, reduced arterial oxygen tension. Moreover, the cognitive impairment resulting from OSA, hypopnea, and UARS puts those afflicted at elevated risk of accidents.

The pathogenesis of the airway obstruction that characterizes OSA, hypopnea, and UARS can include both anatomic and functional abnormalities of the upper airway that result in increased air flow resistance and/or obstruction of air flow. Such abnormalities may include narrowing of the upper airway due to suction forces created during inspiration, the effect of gravity pulling the tongue back to appose the pharyngeal wall, and insufficient muscle tone in the upper airway dilator muscles, among others. It is also believed that excessive soft tissue in the anterior and lateral neck, as commonly observed in obese persons, can apply sufficient pressure to internal structures to narrow the upper airway and restrict air flow.

Conventional treatment of OSA, hypopnea, and UARS has included surgical intervention, such as uvalopalotopharyngoplasty, gastric surgery for obesity, mandibular advancement procedures, maxillo-facial reconstruction, and tracheostomy. However, surgery potentially involves considerable risk of post-operative morbidity and mortality. In addition, the failure rate of surgery is disturbingly high. Pharmacological therapy has also been proposed to treat OSA, hypopnea, and UARS; however, results have been generally disappointing.

Continuous positive airway pressure (CPAP) or bi-level positive airway pressure applied during sleep is commonly used to treat OSA, hypopnea, and UARS patients. Positive pressure is applied to the upper airway to splint or support the airway, thereby preventing its collapse and the resultant airway obstruction. A typical PAP device comprises a flow generator (e.g., a blower) that delivers gas via a delivery conduit to a patient interface. It is also known to deliver the PAP as a continuous positive airway pressure (CPAP), a variable airway pressure, such as a bi-level pressure that varies with the patient's respiratory cycle or an auto-titrating pressure that varies with the monitored condition of the patient. Pressure support therapies are also provided to treat other medical and respiratory disorders, such as Cheynes-Stokes respiration, congestive heart failure, and stroke.

Many patient interfaces are well known in the art. For instance, masks which provide a seal between the compressed air and the patient are common in the art. These interfaces include prongs which fit into the nares of the patient, nasal masks which fit over the patient's nose, and full face masks which fit over the patient's nose and mouth. Although these devices work effectively, they may be uncomfortable for some patients. Moreover, proper fit is often dependent upon the particular user's facial characteristics.

Other patient interfaces have been suggested to deliver positive pressure to a patient that do not depend upon the external facial characteristics of the patient. One such device exemplary of the art is disclosed in U.S. Pat. No. 6,679,257. This device is an oral appliance that is connected to a pressurized gas source, and has a vestibular shield located between the teeth and lips/cheeks of the patient. An oval-shaped tube extends through the shield and into the patient's oral cavity. The oral appliance also includes second shield, or flap, which fits inside the patient's mouth to seal the oral cavity.

Although this device has advanced the art, it also has several drawbacks. For instance, this oral appliance is not securely registered in the patient's mouth. Thus, it could move around and ultimately compromise the seal between the appliance and the patient. Secondly, the device is configured to deliver positive pressure to the patient's airway. As discussed above, positive pressure may be uncomfortable for some patients and interfere with normal breathing.

Another way to retain the patient's airway open is through the use of negative pressure. It has been found that negative pressure may be applied to the patient's oral cavity to draw the patient's soft palate and tongue away from the rear pharyngeal wall. As the soft palate is drawn forward, it seals against the rear portion of the tongue while simultaneously keeping the airway open. U.S. Pat. No. 5,957,133 discloses an oral appliance capable of creating a subatmospheric environment within the patient's mouth. The oral appliance disclosed in this reference has a hollow body with an opening in the rear of the device. The device is connected to a negative pressure vacuum.

Even though this device advances the art, it can be further improved upon. Registration and proper alignment of the device is achieved by dental impressions which must be custom molded in a thermal set material. However, merely opening ones mouth, or yawning during sleep, would be sufficient to undermine this method of registration. Secondly, the appliance provides an opening in the rear of the device to draw the patient's tongue and soft palate away from the posterior pharyngeal wall. However, it does not provide a barrier to prevent other soft tissue, such as the patient's cheeks, from being drawn inward towards the opening and causing discomfort to the user.

Another drawback to this device is that while suction is applied to the device the soft tissue may be drawn towards the opening of the device and partially, or completely, occlude the rear opening of the device. As a result, soft tissue damage can occur due to prolonged suction force. Secondly, while the opening is occluded, the device will be rendered ineffective since it is no longer in fluid communication with the retroglossal area. Yet, another drawback to this device is that it fills a majority of the oral cavity. By reducing the oral volume in the patient's mouth, it impedes anterior movement of the tongue and soft palate to unblock the airway. Accordingly, it would be desirable to have an oral device which is configured to create a negative pressure environment within a patient's oral cavity. It would be further desirable to have an oral appliance that is configured to securely register within a patient's oral cavity. It would also be desirable to have an oral appliance that is configured to prevent soft tissue from being drawn inwardly and causing discomfort to the patient. It would be still further desirable to have an oral appliance that is designed to maximize the available oral volume to enhance comfort and allow the tongue and soft palate to be drawn anteriorly by the applied negative pressure.

SUMMARY OF THE INVENTION

In accordance with the broad teachings of the invention, an oral appliance is disclosed that is connected to a negative pressure supply via a conduit to create a negative pressure environment within the user's oral cavity. The oral appliance has a first portion and a second portion. The first portion includes a channel that is configured to receive the user's teeth. At least one opening is formed in the channel such that the opening faces towards the user's teeth and gums. The oral appliance also includes a second portion. The second portion is connected to the negative pressure device and has an internal lumen to deliver the negative pressure to the user's oral cavity via the openings.

In another aspect of the invention, an oral appliance is disclosed that has a first portion and a second portion. The first portion includes a channel that is configured to receive the user's teeth. At least one opening is formed in the channel such that the opening faces towards the user's teeth and gums. The oral appliance also includes a second portion. Located within the second portion is a negative pressure supply. The negative pressure supply is in fluid communication with the user's oral cavity via the openings to create the subatmospheric pressure environment.

In another aspect of the invention, an oral appliance is connected to the negative pressure oral device. The oral appliance includes a first portion and a second portion. The first portion includes a member having a passageway. The second portion has an internal lumen in communication with the passageway. Together the passageway and internal lumen operate to communicate the negative pressure generated by the negative pressure device to the user.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

BRIEF DESCRIPTION OF THE DRAWINGS

FIG. 18b is a side elevational view of the embodiment shown in FIG. 18a;

FIG. 19b is a side perspective view of the embodiment shown in FIG. 19a.

DETAILED DESCRIPTION OF THE EXEMPLARY EMBODIMENTS

Figure 1:
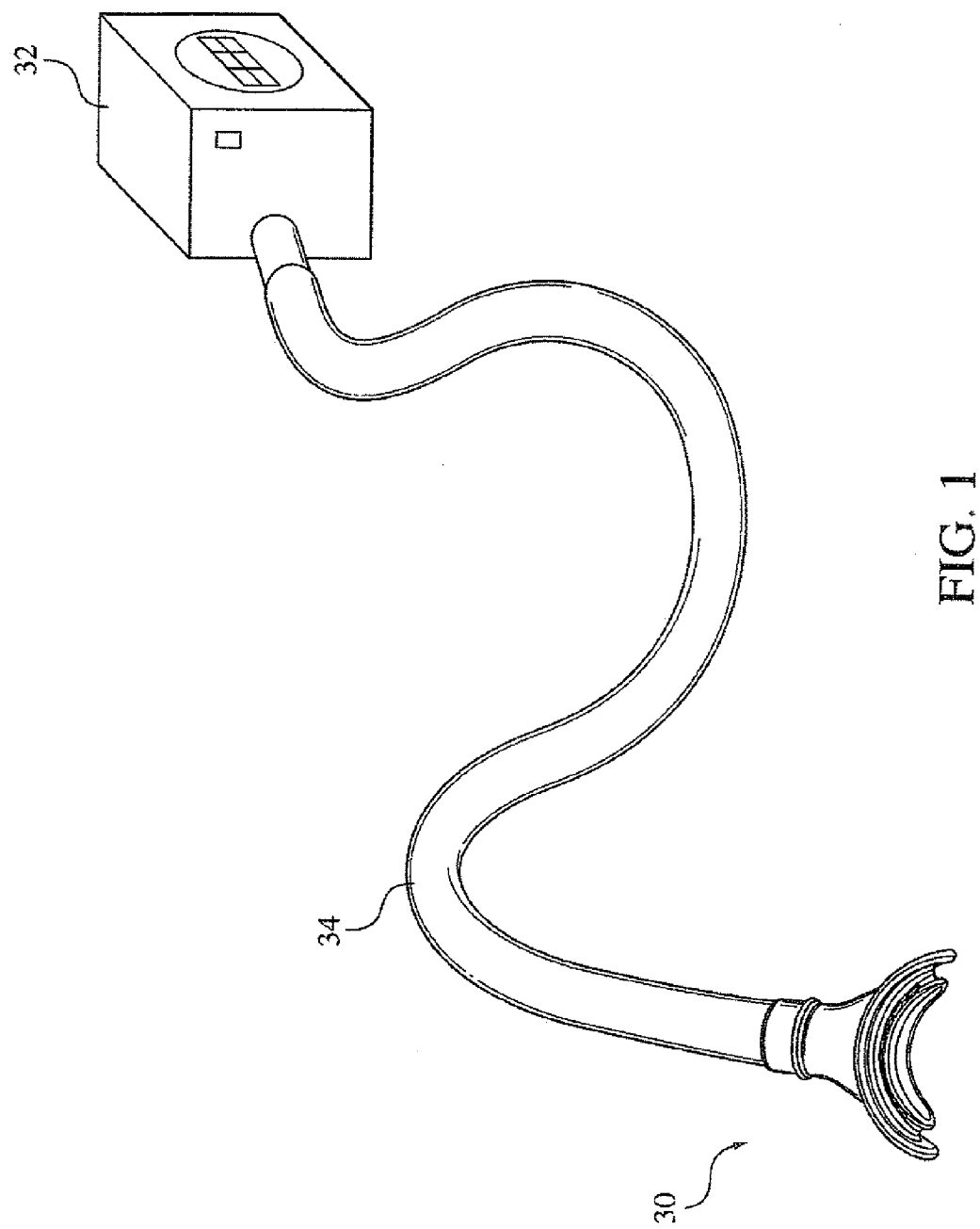
FIG. 1 is perspective view of an assembly including the oral appliance, conduit, and negative pressure supply of the present invention.
Figure 2:
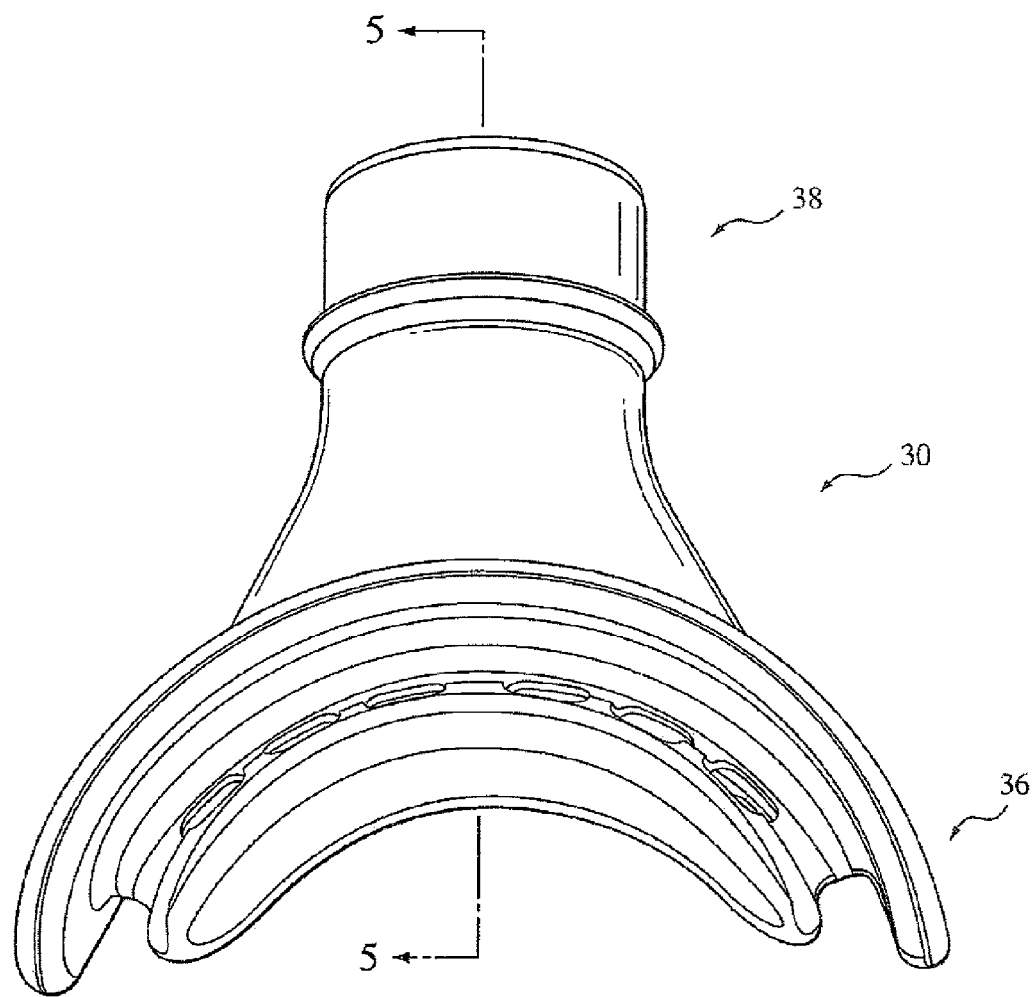
FIG. 2 is a top perspective view of the oral appliance of the present invention.

FIG. 1 schematically illustrates an exemplary embodiment of oral appliance 30 connected to a negative pressure supply 32 via a conduit 34. As seen in FIG. 2, oral appliance 30 includes a first portion 36 and a second portion 38. The first portion and the second portion may be formed separately and connected together.

The first portion is formed from a flexible material such as a silicone molding compound. A flexible material provides comfort to the user. The durometer (hardness) of the material is chosen to provide sufficient rigidity so the internal cavity does not collapse from the negative air pressure or from external pressure applied from the teeth.

The second portion is formed from a rigid material such as Polycarbonate. The use of a rigid material provides support for the deformable material. First portion 36 and second portion 38 may be separate parts coupled together or the first portion 36 may be overmolded onto the second portion. Alternatively, first portion 36 and second portion 38 may be formed together integrally from a single material. The present invention also contemplates incorporating an antimicrobial, antibacterial, and antifungal chemical additives into the first portion 36 and/or second portion 38 such as the chemical additive sold under the trademark MICROBAN™ by Microban Products Company.

Figure 3:
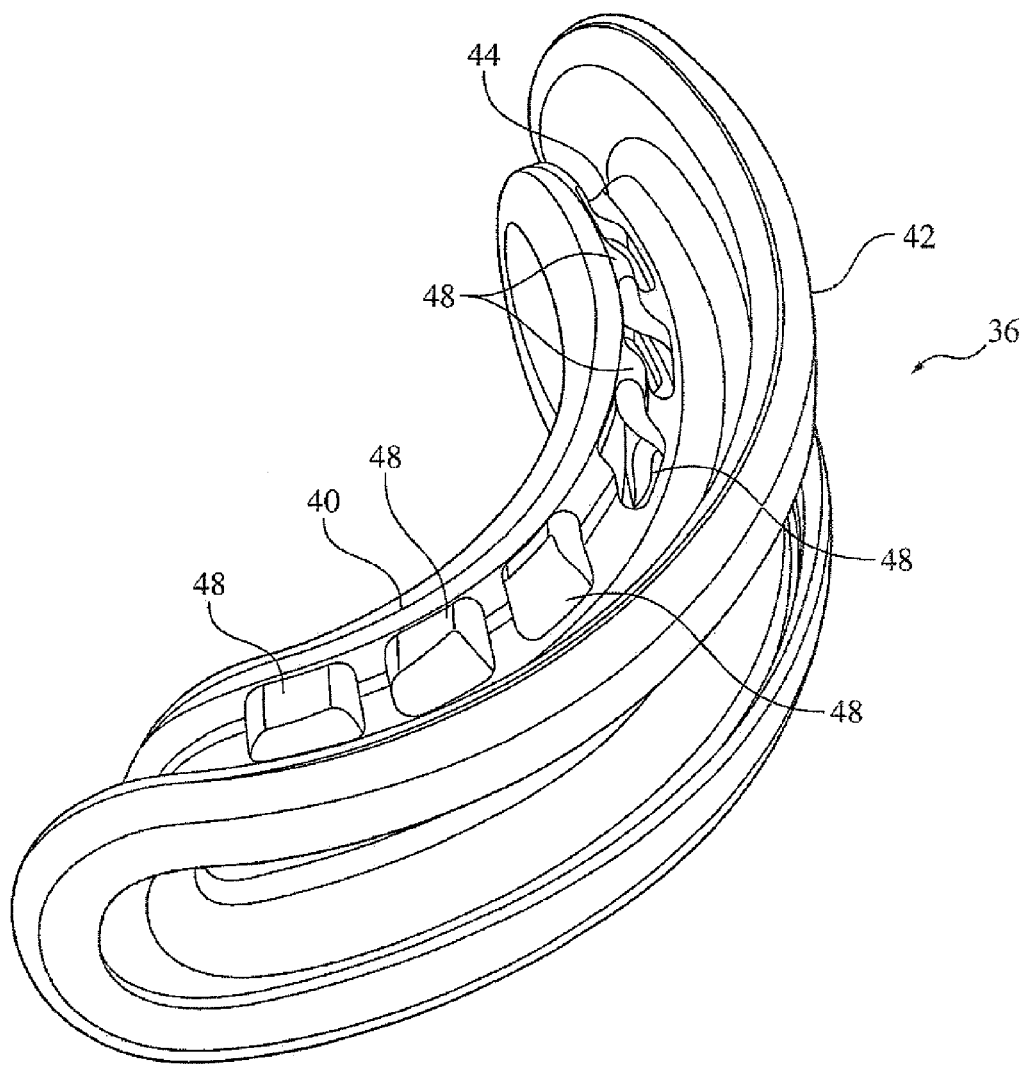
FIG. 3 is a front perspective view of a first portion of the oral appliance.
Figure 5:
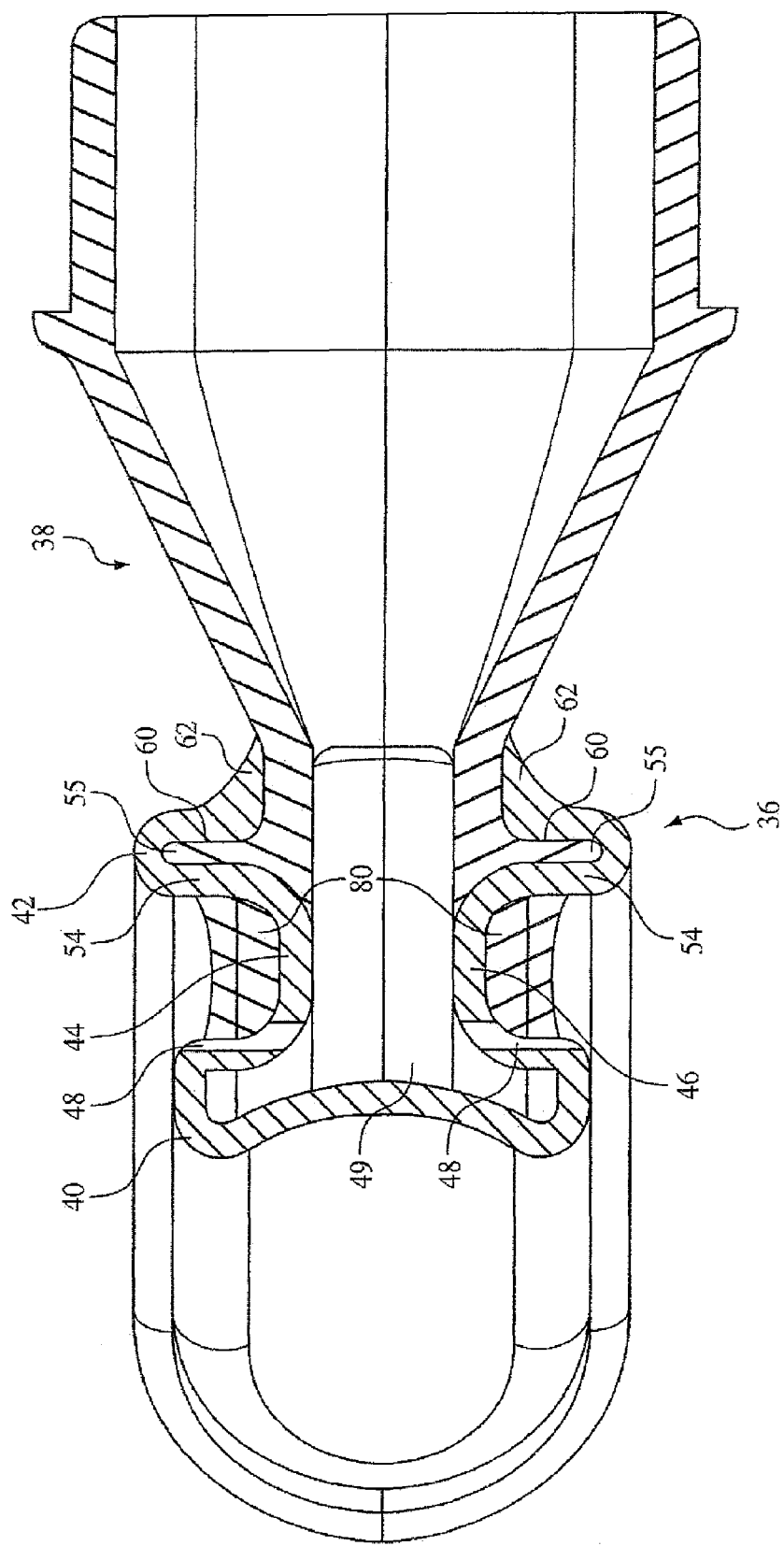
FIG. 5 is a side cross-sectional view of the oral appliance cut along line 5-5 of FIG. 2.

Turning now to FIG. 3, first portion 36 has an inner peripheral ridge 40 and an outer peripheral ridge 42 defining a first channel 44 and a second channel 46 (shown in FIG. 5). First channel 44 and second channel 46 have a plurality of apertures 48 in communication with one another via internal cavity 49. The unique location of the apertures permits the negative pressure environment to be created while minimizing the suctioning of soft tissue because the apertures are located proximate to rigid tissue in the user's oral cavity such as the teeth and gums. Further, the aperture(s) and channels distribute the negative pressure over a wide area of the mouth so that even if the apertures in a particular region become plugged by soft tissue the oral appliance will continue to work effectively by using the remaining open apertures. Secondly, the use of multiple apertures ensures that negative pressure is evenly distributed about the user's oral cavity.

The first portion is configured to fit within the user's mouth with the inner peripheral ridge just inside the user's teeth and the outer peripheral ridge just outside the user's teeth. This configuration utilizes features of the user's oral geometry to positively register oral appliance 30 in place. Registration of the device is further enhanced through the form fitting characteristics when a deformable material is utilized to construct the first portion.

Figure 4:
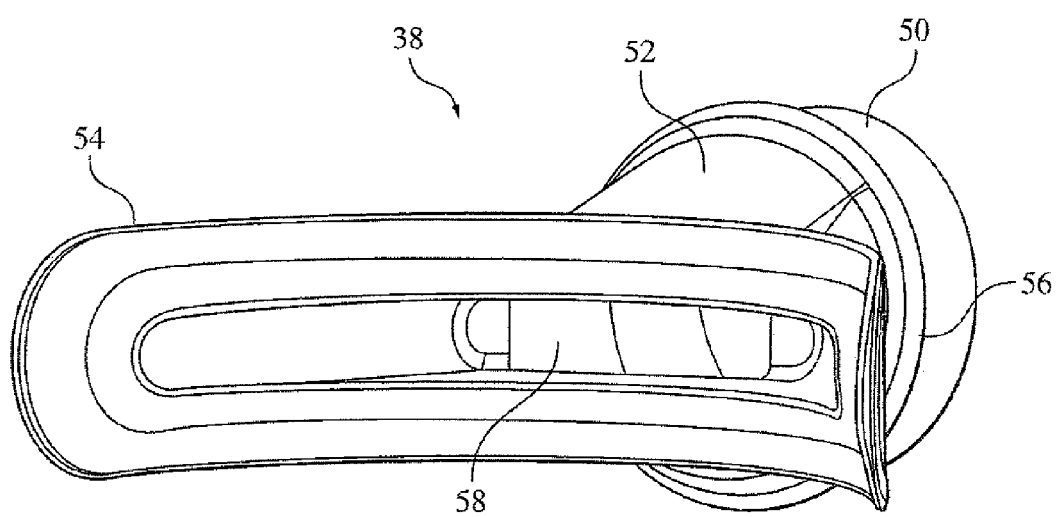
FIG. 4 is a rear perspective view of a second portion of the oral appliance.

As seen in FIG. 4, second portion 38 includes a conduit interface portion 50 leading to a transitional portion 52, which in turn leads to a coupling portion 54. As shown in FIG. 5, the coupling portion 54 is a circumferential rib 55. The second portion also includes an annular ring 56 about conduit portion 50 and acts as an abutment surface for conduit 34. Second portion 38 has an internal lumen 58 providing communication between the negative pressure supply and the apertures 48 of the first portion 36 via internal cavity 49.

With reference to FIG. 5, second portion 38 fits inside first portion 36. First portion 36 includes an internal groove 60 that is sized and shaped to receive coupling portion 54. By inserting coupling portion 54 inside internal groove 60, the oral appliance is provided with internal rigidity while presenting a deformable and comfortable surface within the user's oral cavity. The first portion 36 may be formed having a fillet 62 about outer ridge 42 to provide a comfortable surface for the inside of the user's lip to rest against. This feature provides yet another mechanism to positively register the oral appliance of the present invention within the oral cavity of the user.

Figure 6:
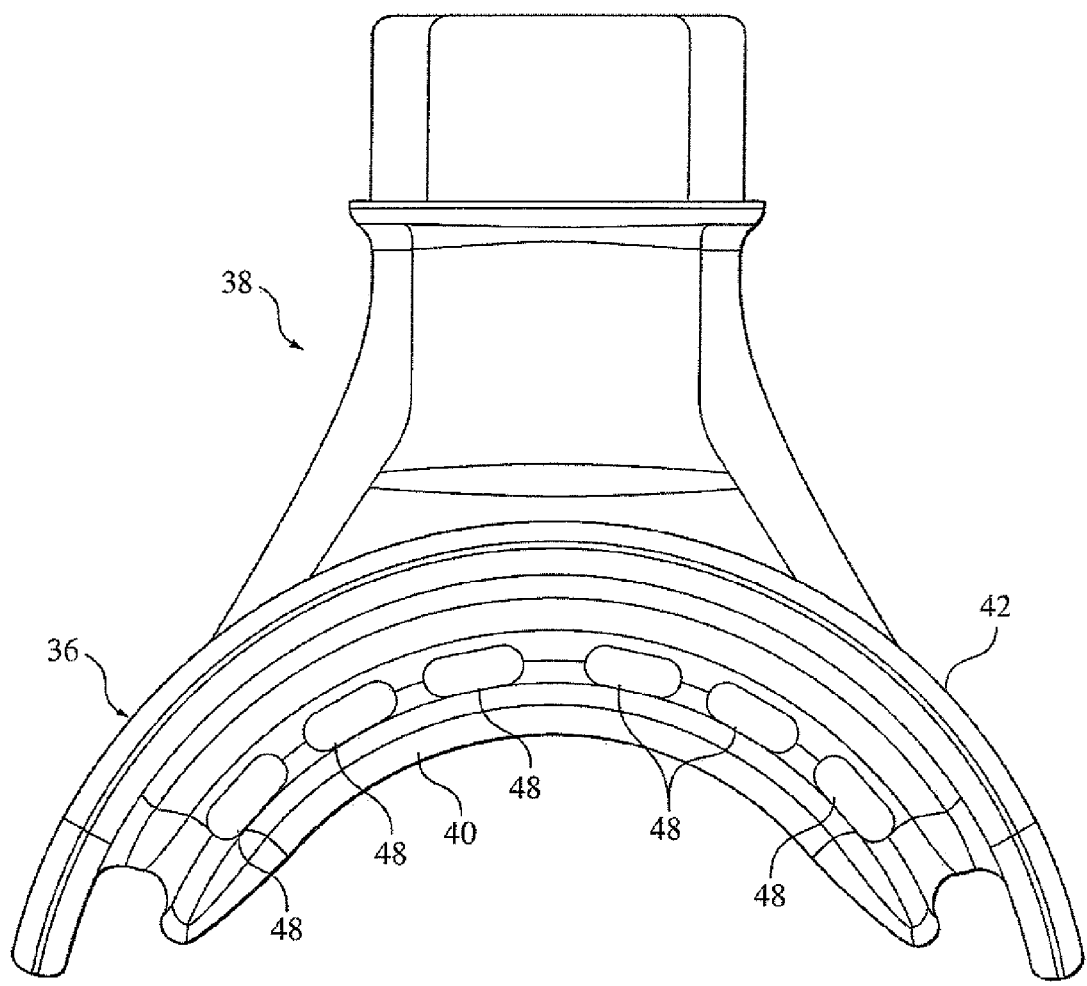
FIG. 6 is a top plan view of the oral appliance.

As best appreciated with reference to FIG. 6, outer ridge 42 provides a barrier to further isolate the negative pressure environment created within the user's mouth and the user's cheeks. Without the barrier formed by outer ridge 42, the user's cheeks would be drawn inwardly and cause discomfort to the user. The suction forces exerted upon outer ridge 42 are resisted by the rigidity of coupling portion 54.

Figure 7:
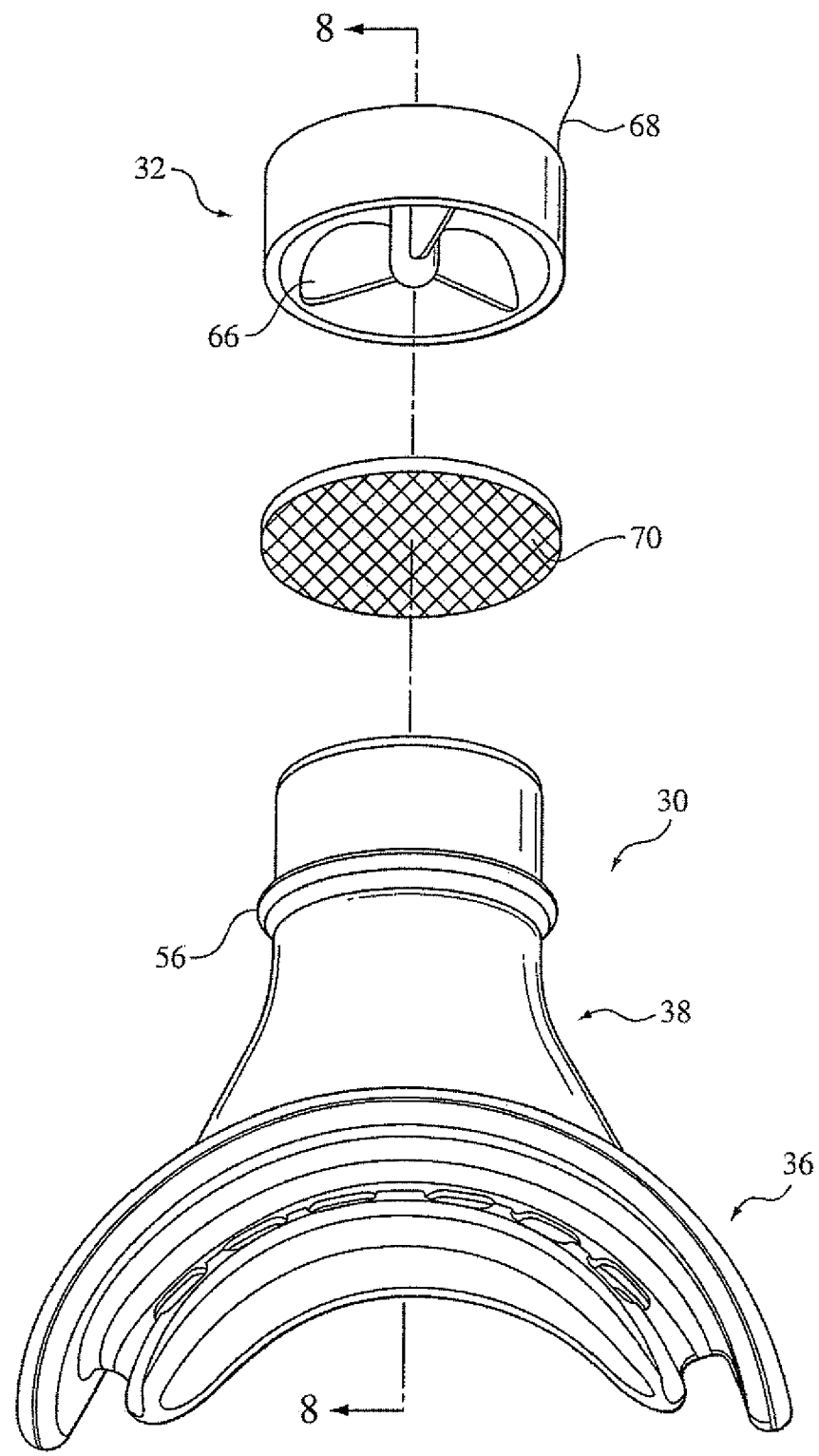
FIG. 7 is an exploded perspective view of the oral appliance of a first alternative embodiment of the present invention.
Figure 8:
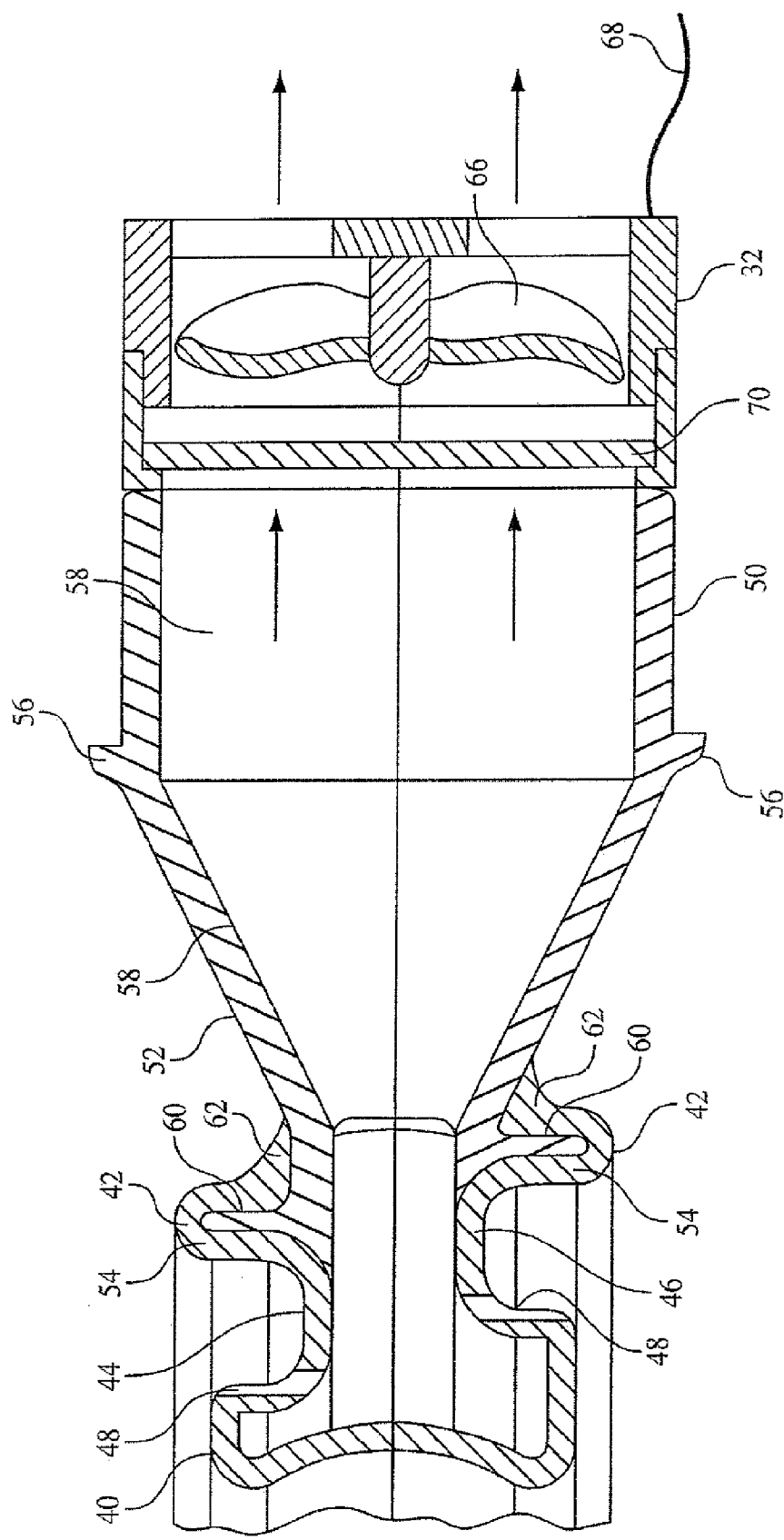
FIG. 8 is a cross-sectional view of the oral appliance cut along line 8-8 of FIG. 7.

In an alternative embodiment, as shown in FIGS. 7 and 8, the second portion 38 may house the negative pressure environment. Negative pressure supply 32 may be any device capable of reducing the pressure within the user's oral cavity such as piston, turbine, or axial screw type vacuum pumps. As seen in FIG. 7, negative pressure supply 32 includes a turbine 66 which is driven by an external power supply, not shown connected via insulated leads 68. This embodiment of the invention enhances the comfort and transportability of the device. Second portion 38 also includes a filter 70. The filter prevents fluid from being drawn into the negative pressure supply 32. One additional unique aspect of this embodiment of the present invention is that first channel 44 may be offset relative to second channel 46 to provide mandibular advancement as seen in FIG. 8. The degree of offset can be varied as needed for a particular user.

Figure 9:
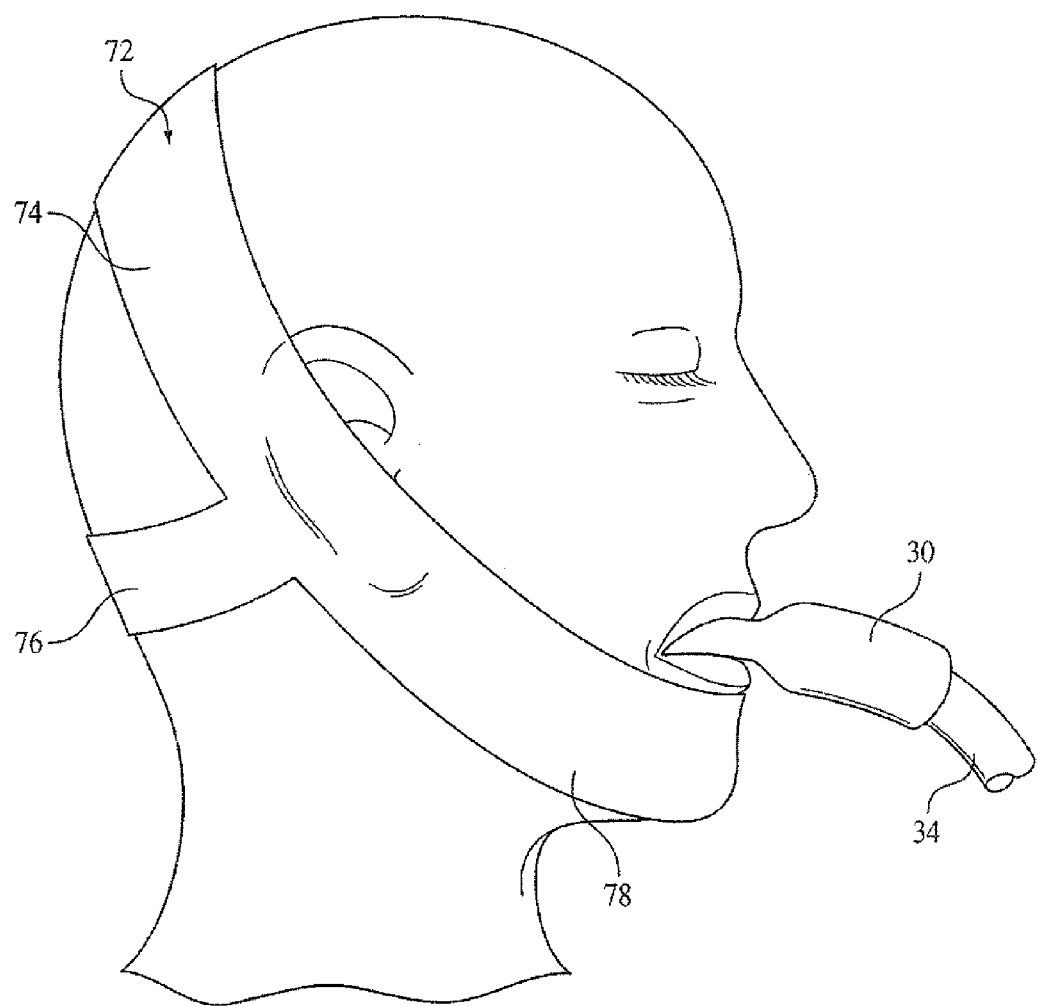
FIG. 9 is a side elevational view of the oral appliance and a chin strap in use on a user.

Oral appliance 30 may also be used in combination with a chin strap 72 as shown in FIG. 9. Chin strap 72 includes a head portion 74, a neck portion 76 and a chin portion 78. Chin strap 72 is formed from an elastic material. Preferably, the chin strap is formed from neoprene, braided elastic fabric, or other similar materials. As is well known in the art, the chin strap will support the user's jaw and assist in keeping the user's mouth closed. Often, users inadvertently open their mouth while asleep. The chin strap will assist such users in keeping their mouth closed and thus maintain the negative pressure environment.

Figure 10:
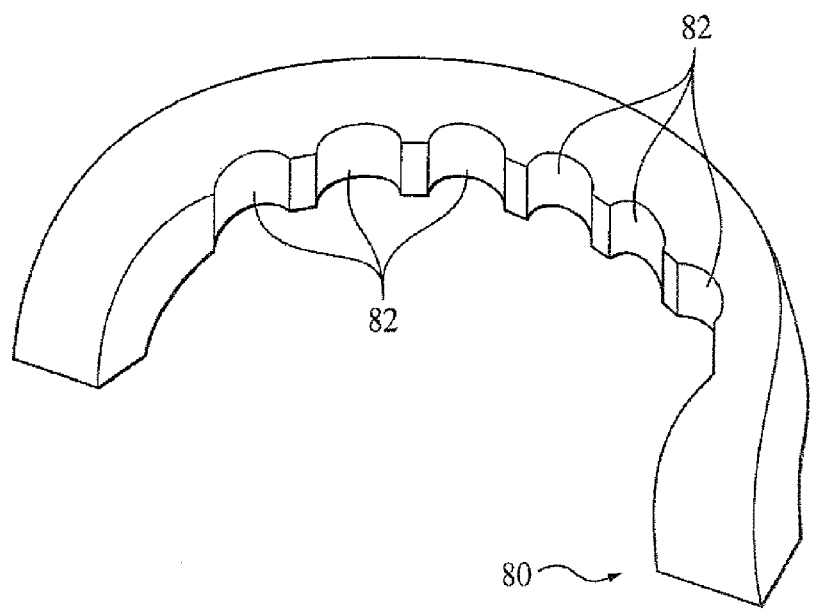
FIG. 10 is a top perspective view of a third portion of a second alternative embodiment of the present invention.

In yet another alternative embodiment, oral appliance 30 may also include a third portion 80 as shown in FIG. 10. The third portion is fitted into first channel 44 and second channel 46 and includes scallops 82 that correspond to apertures 48. The purpose of the third portion is to provide enhanced registration of oral appliance 30 in the user's mouth by closely conforming to the outer geometry of the user's teeth. Third portion is formed from a deformable thermal-set material. Preferably, the material is Ethylene-Vinyl-Acetate (EVA). When heated, the material softens and is inserted into the user's mouth to take an imprint of the user's particular oral characteristics, as is well known in the art. Once the softened material has been molded to the user's oral characteristics it is cooled to hold this shape.

Figure 11:
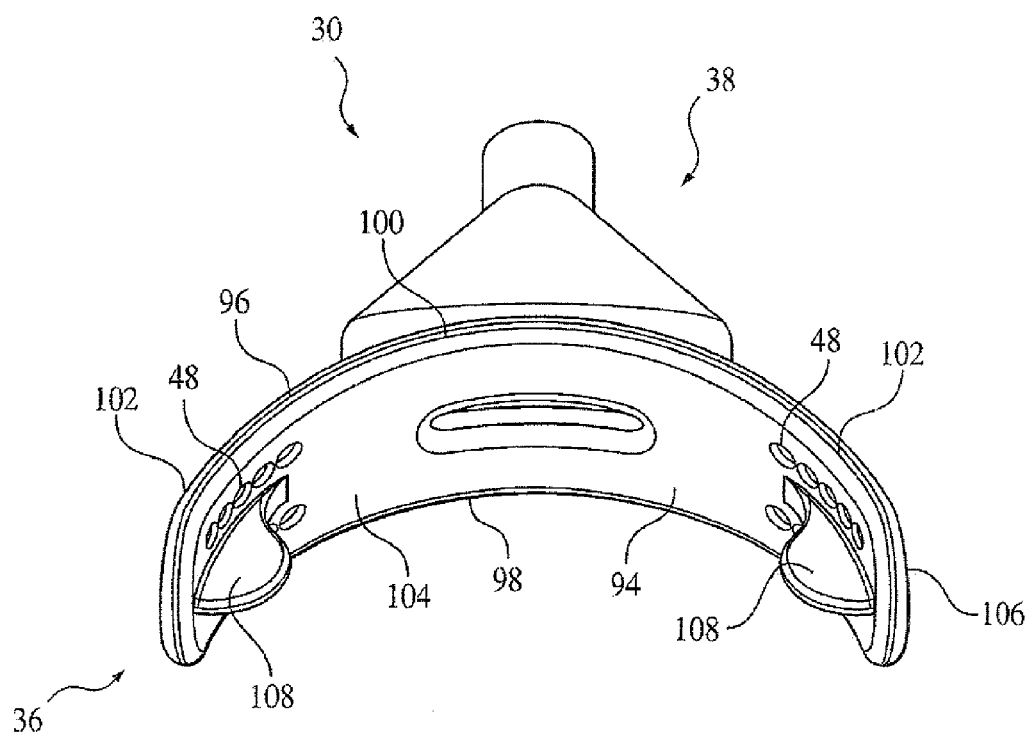
FIG. 11 is a rear perspective view of a third alternative embodiment of the present invention.

As shown in FIG. 11, in still another embodiment, oral appliance 30 has a first portion 36 and a second portion 38. The first portion and second portion are formed together as a single unitary piece. However, one skilled in the art can best appreciate that first portion 36 and second portion 38 could be formed separately. The first portion, of this embodiment, includes a member 94. The member 94 has a generally arcuate shape to conform to the shape of the user's mouth. Of course the size (including but not limited to the length, width, and height of the member) and shape of this device could be altered to accommodate the oral cavity of various users. Member 94 includes a median portion 100 bounded by distal portions 102. The member also includes an inner surface 104 and an outer surface 106. The inner surface 104 and outer surface 106 are connected together via a top edge 96 and a bottom edge 98.

This embodiment includes a pair of projections 108. Projections 108 serve as a support or wedge between the user's teeth so that the user's teeth remain distanced apart and also assists with proper registration of the device. Projections 108 have a generally rounded configuration so that the device does not present sharp edges that could cause discomfort to the user. The projections could be formed anywhere along member 94. As shown in FIG. 11, projections 108 extend from the distal portions 102. This location of the projections provides some unique advantages. When properly located in the user's mouth, the projections are located rearward in the user's mouth at or near the location of the user's molar teeth. The user's molars tend to provide a flatter bottom surface against which the projections 108 can register thereby providing a more stable surface and better registration of the device in the user's mouth. Projections 108 act to wedge or splint the user's teeth apart a distance. Of course, the distance that the upper and lower teeth are separated from one another can be altered by increasing or decreasing the size of these projections. Alternatively, the inventors of the present invention also contemplate that projections 108 could be omitted. In this embodiment, registration of the device would be accomplished by one or more of the other structures present in the device such as member 94.

As is well known in the art, a hinge is created between the mandible and temporal bone of the user's head. By locating the projections closer to the hinge rather than towards the front of the user's mouth, the size of the projections may be reduced. Of course projections 108 could extend from some other location closer to, or from, median portion 100. However, such a configuration would require a larger projection to achieve the same spacing between the user's upper and lower teeth. Accordingly, one can appreciate that by locating the projections on, or near, the distal portions of the oral appliance results in a device that provides more comfort for the user while utilizing less material.

Figure 12:
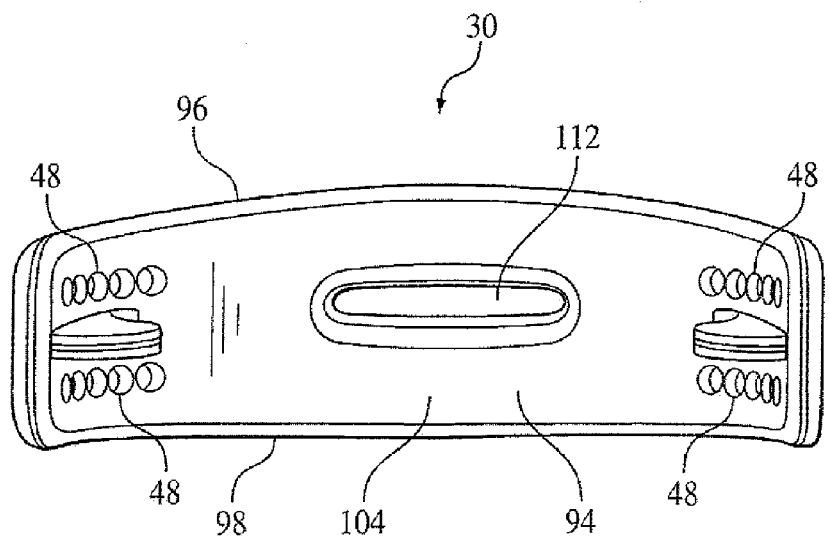
FIG. 12 is a rear elevational view.

The oral device also includes apertures 48. The apertures are in fluid communication with the negative pressure supply 32. The apertures are located to face towards hard or rigid tissue, such as the user's teeth and gums in the user's mouth to minimize the potential for occlusion of the apertures by sucking soft tissue into the apertures. Once again, the apertures could be located in a variety of locations along the first portion 36. However, it has been found that by locating the apertures further rearward in the user's mouth assist in creating the negative pressure environment desired to draw the user's tongue forward. The present invention contemplates that the apertures could be located elsewhere. However, in the event that the apertures are located forward in the user's mouth towards the user's lips may result is a loss of pressure requiring the application of additional negative pressure in order to achieve the desired therapeutic result to compensate for these losses or additional measures would need to be taken to minimize this loss of negative pressure. In FIG. 12 the apertures are five cylindrical holes above each projection and five cylindrical holes below each projection 108. Of course, the number, size, shape and distribution of these apertures can be altered without departing from the scope of the present invention.

As best appreciated with reference to FIG. 12, the oral appliance also includes a depression or cavity 112. In this embodiment, the cavity provides a receptacle to receive at least a portion of the user's tongue. When negative pressure is applied to the oral appliance located inside the user's mouth, a negative pressure environment is created. As a result the user's tongue will tend to be drawn forward. In the prior embodiments, this forward movement, in some users, may be partially impeded by inner peripheral ridge 40. In this embodiment, by splinting the user's upper and lower teeth apart a distance with projections 108 and providing a cavity 112 into which the user's tongue may fit, there are less impediments that may impede the user's tongue being drawn forward. Depending on the characteristics of the particular user, the user's tongue may project beyond the user's teeth or even beyond the user's lips without compromising the negative pressure environment created by the oral appliance in the user's mouth and enhance the therapeutic result achieved by this device.

As another alternative embodiment, the inventors contemplate that it may also be useful to add additional openings 114 in addition to apertures 48 proximate soft tissue such as proximate the user's cheeks or gums to assist in securing the device in place. The inventors contemplate that the soft tissue will substantially occlude these openings 114 and thus not substantially inhibit the ability of apertures 48 to create a negative pressure environment within the user's mouth while providing the additional benefit of securing the device within the user's mouth. In addition, an opening 114 can be used to clean the interior of the device. The inventors contemplate that it may be desirable to terminate passageway 120 at an aperture 48, rather than continuing through the entire member to assist in easily expelling foreign objects that may have collected in passageway. Alternatively, an opening 114 could be formed on or near the distal portion of the member fitted with a cap or seal, not shown, to seal the interior of the device when in use. When it is desired to clean the device, the cap can be removed to provide easy cleaning. The opening used for cleaning could be situated anywhere along the member to provide access to the interior. The number, size, shape or location of the openings 114 can be modified without departing from the scope of the present invention.

Figure 13:
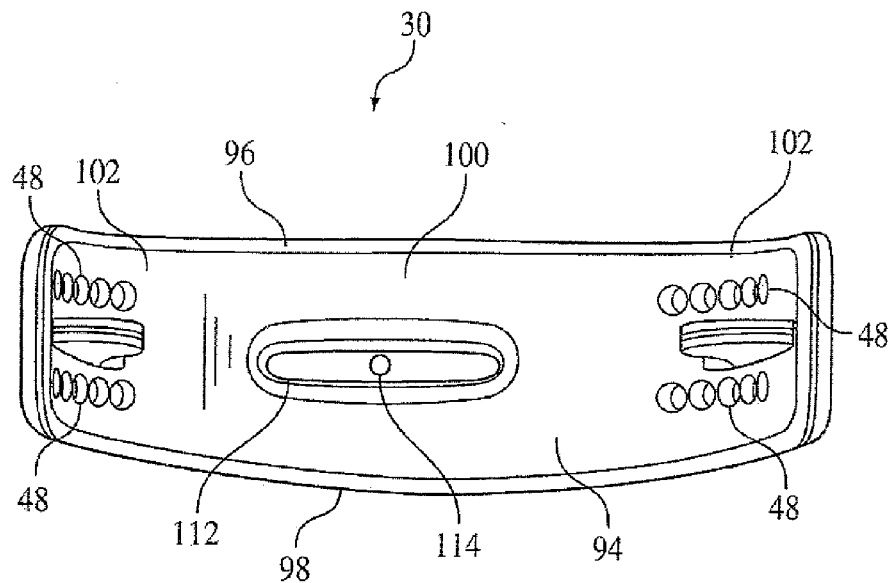
FIG. 13 is a rear perspective view of a fourth alternative embodiment.

In one non-limiting example, cavity 112 could include an opening 114, as seen in FIG. 13, to apply negative pressure directly to the user's tongue. Once the user's tongue has been drawn forward, the negative pressure created by an aperture located in this region could be used to secure the user's tongue in place and provide further retention of the user's tongue in a forward orientation. The size and shape of the cavity may be altered to accommodate the particular characteristics of the user's tongue. In another aspect, opening 114 could include a one-way valve so that positive pressure created in the event that the user's tongue plugs the cavity can be expelled without compromising the negative pressure environment. The one-way valve may be in fluid communication with the negative pressure supply 32. Alternatively, the one-way valve could be in communication with the external environment. In the event that a negative pressure environment is created inside cavity 112, the user's tongue could isolate this negative pressure environment by sealing against the edges of cavity 114. If this does occur, the cavity would provide additional negative pressure to either supplement or substitute for the negative pressure created by the negative pressure supply.

When a one-way valve is used, the space between the user's tongue and cavity may retain a negative pressure environment and thus keep the user's tongue in a forward orientation in the event that the negative pressure environment created by the negative pressure supply 32 ceases to exist. This could occur under a variety of circumstances such as power failure or mechanical failure of negative pressure supply 32, mechanical failure or inadvertent disconnection of conduit 34, or mechanical failure of oral device 30. In addition, the negative pressure environment created inside the user's mouth could also be compromised simply by the user opening their mouth, or the use of an oral device that does not fit properly.

Figure 14:
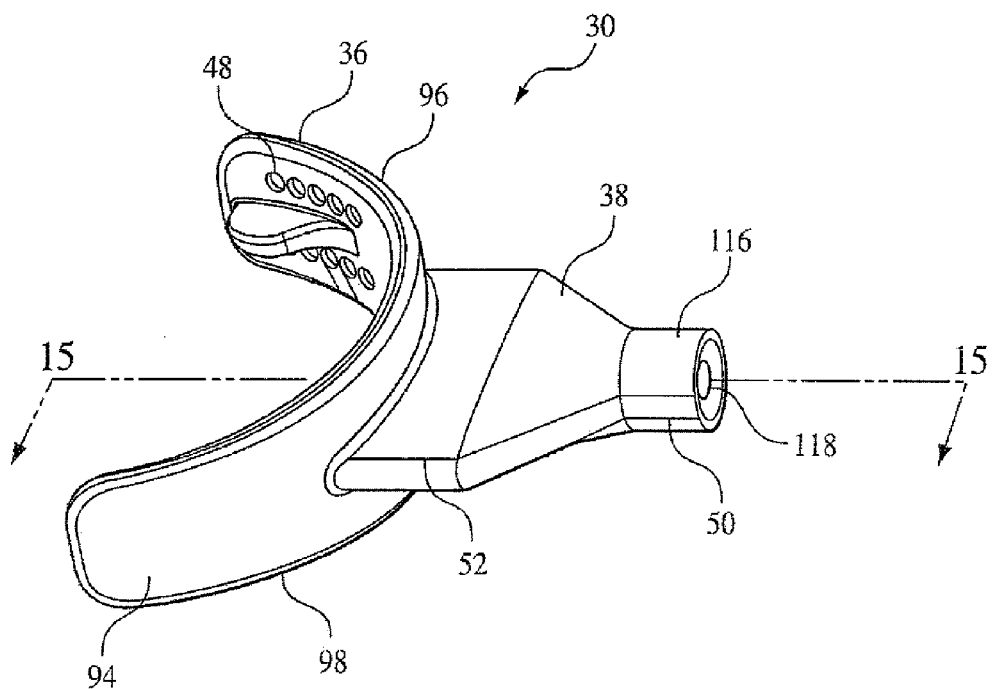
FIG. 14 is a side perspective view.
Figure 15:
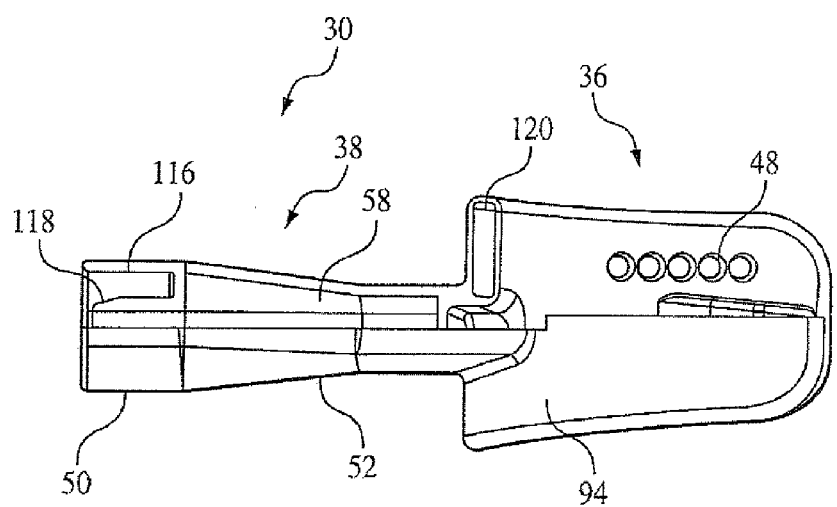
FIG. 15 is a partial cross-sectional view along line 15-15 of FIG. 14.

Oral appliance 30 also includes a second portion 38 as best appreciated with reference to FIGS. 14, and 15. As seen in FIG. 14, second portion 38 includes a conduit interface portion 50 connected to a transition portion 52 which connects to the outer surface 106 of first portion 38. The conduit interface portion 50 includes a sleeve 116 and centrally disposed coupling 118. Conduit 34 is fitted into sleeve 116 and over coupling 118 to provide a substantially air tight seal between the negative pressure supply. Coupling 118 has a barb or tip-like configuration. However, a variety of couplings are well known in the art. The conduit interface portion 50 or transition portion 52 may be offset either towards the top edge 96 or bottom edge of first portion 36 in order to accommodate the particular oral configuration of various users.

During sleep, many users' lips do no align with their front teeth. Therefore, the inventors of the present application contemplate that the negative pressure environment and comfort of this device can be enhanced by offsetting the conduit interface 50 or transition portion 52 relative to the first portion 36. The second portion 38 provides a substantially air tight coupling between conduit 34 and first portion 36 via internal lumen 58. Internal lumen 58, in turn, is in fluid communication with apertures 48 via passageway 120 formed in first portion 36. The passageway 36 may be defined by a single conduit. Alternatively, passageway 36 may be separated by one or more walls or ribs into sub-conduits to isolate various apertures 48 from one another. By isolating the various apertures 48 relative to one another, the oral appliance will continue to function properly in the event that some of the apertures or sub-conduits become occluded.

Further, the inventors contemplate that the negative pressure environment may be further enhanced by supplying a headgear assembly or chin strap 72 as shown in FIG. 9. As described in detail above, a chin strap 72 will support the user's jaw and assist in keeping the user's mouth closed. Often, users inadvertently open their mouth while asleep. The chin strap will assist such users in keeping their mouth closed and thus maintain the negative pressure environment.

Figure 16:
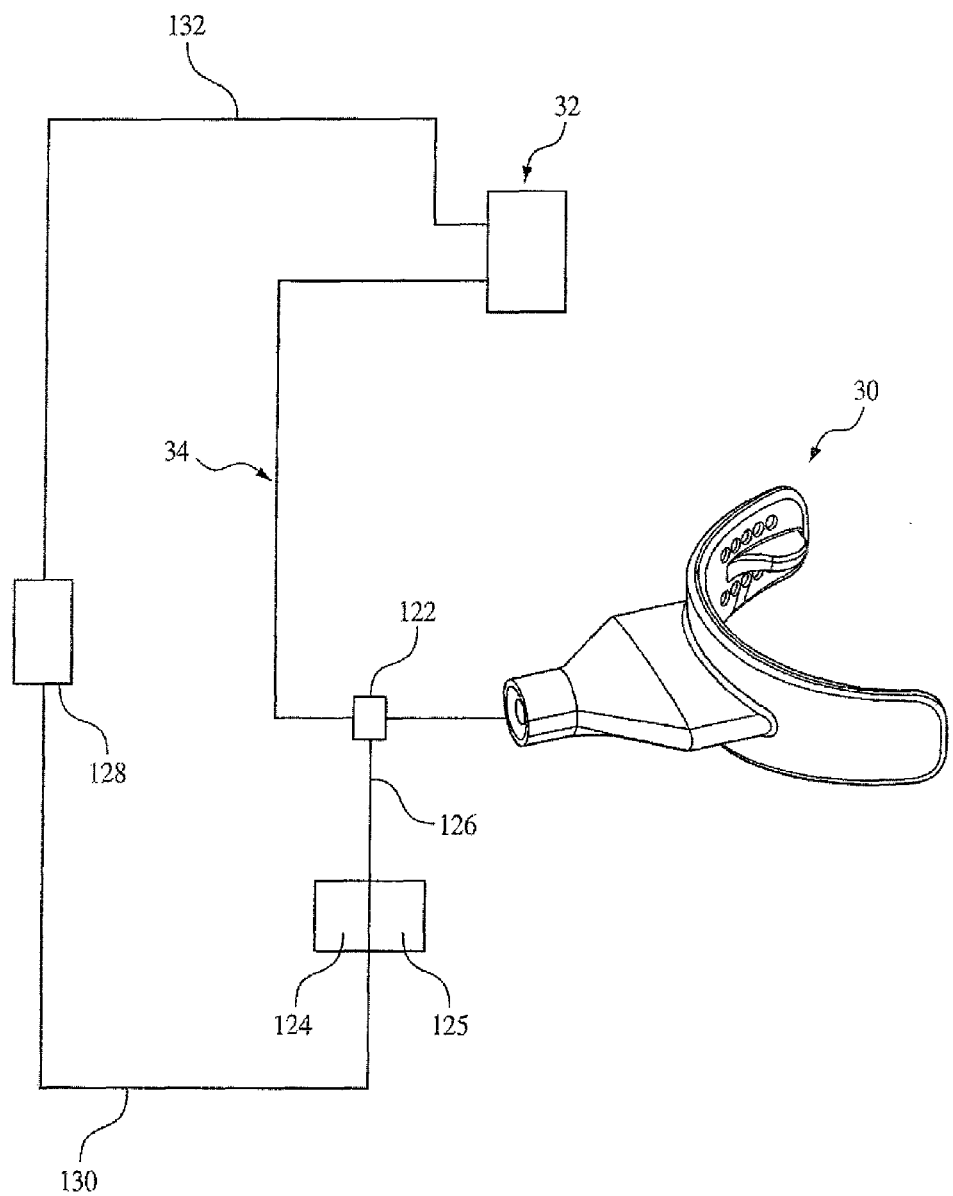
FIG. 16 is a schematic view showing the oral appliance, a pressure sensor, processor, controller, conduit, and negative pressure supply of the present invention.

As best appreciated with reference to FIG. 16, the inventors further contemplate that it may be desirable to incorporate a pressure sensor 122 in the negative pressure supply 32, conduit 34, or oral appliance 30 to detect changes in pressure. A pressure sensor can be used to provide a multitude of additional benefits. For instance, the pressure sensor would be capable of detecting various physiological conditions such as whether the user has ceased to breathe, removed the device, or is snoring. In addition, a pressure sensor can also be used to determine if the device is operating effectively or has become blocked.

The pressure sensor 122 is operatively connected to a processor 124 via a first link 126. A signal is communicated to the processor 124 via the first link. The processor may analyze and store the signals received from the pressure sensor in memory 125. In addition, the processor may transmit a signal to a controller 128. The controller is connected to the processor via a second link 130 and to the negative pressure supply 32 via a third link 132. One skilled in the art can best appreciate that controller 128, processor 124, memory 125, pressure sensor 122, and negative pressure supply 32 may be commonly housed or separate components operatively connected together. In addition, links 126, 130, and 132 may be an electrical connection such a wire. Alternatively, links 126, 130, 132 may be wireless thereby transmitting the signals over any one of a variety of well know wireless technologies such as RF, IR, and the like.

Figure 17:
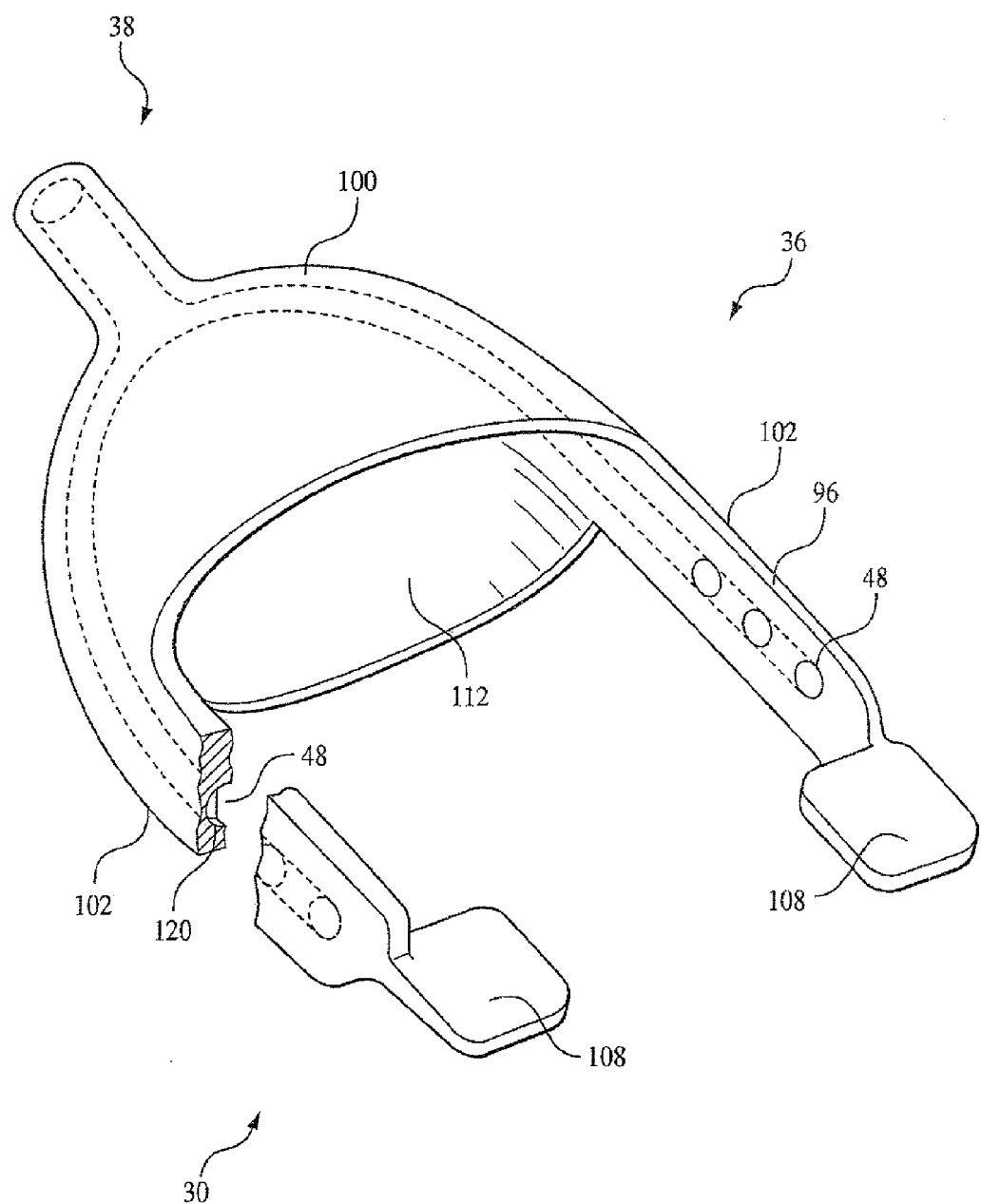
FIG. 17 is a fifth alternative embodiment of the present invention with a partial cut away showing passageway 120.

In yet a further alternative embodiment, an oral appliance 30 is shown in FIG. 17 with an oral device having a cavity 112 for receipt of the user's tongue. The cavity of this embodiment is comparatively large relative to the prior embodiments to further enhance the capability of the user's tongue to be drawn forward due to the negative pressure supply. Another unique feature of the embodiment shown in FIG. 17 is that projections 108 are formed as part of distal portions 102 rather than extending from inner surface 104.

Moreover, projections 108 extend from bottom edge 98 of oral appliance 30. As discussed above, offsetting first portion 36 relative to second portion 38 provides enhanced comfort for some users since it has been found that during sleep a user's lips and teeth often do not align. One way to adjust the alignment of the device is by offsetting conduit interface portion 50 and transition portion 52 relative to the first portion 36. Alternatively, as in this embodiment, another way to achieve a similar result is to offset projections 108 relative to the second portion 38. In addition, projections 108 are formed closer together than the remainder of distal portions 102.

As discussed above with the prior embodiments, first portion 36 and second portion 38 may also be formed separately which permits different materials for each, or portions thereof, to be chosen that could be formed from differing materials such as projections 108. For instance, rather than utilizing the same material for the first portion 36 and second portion 38, and projections 108, a softer material could be chosen for the first portion, or projections 108, that fit into the user's mouth to provide enhanced comfort while a more rigid material could be selected for the second portion to provide structural rigidity to the oral appliance.

The first portion may also be formed by a moldable material to enhance registration of oral appliance 30 in the user's mouth by closely conforming to the outer geometry of the user's teeth or a separate material could be attached to the first portion proximate the user's teeth. One such thermal set material that could be used in this application is Ethylene-Vinyl-Acetate (EVA). Of course a variety of other thermal set materials could also be used without departing from the scope of the present invention. When heated, the material softens and is inserted into the user's mouth to take an imprint of the user's particular oral characteristics, as is well known in the art. Once the softened material has been molded to the user's oral characteristics it is cooled to hold this shape. In addition, the oral appliance could also include antimicrobial, antibacterial, and antifungal chemical additives such as the chemical additive sold under the trademark MICROBAN™ by Microban Products Company.

Figure 18A:
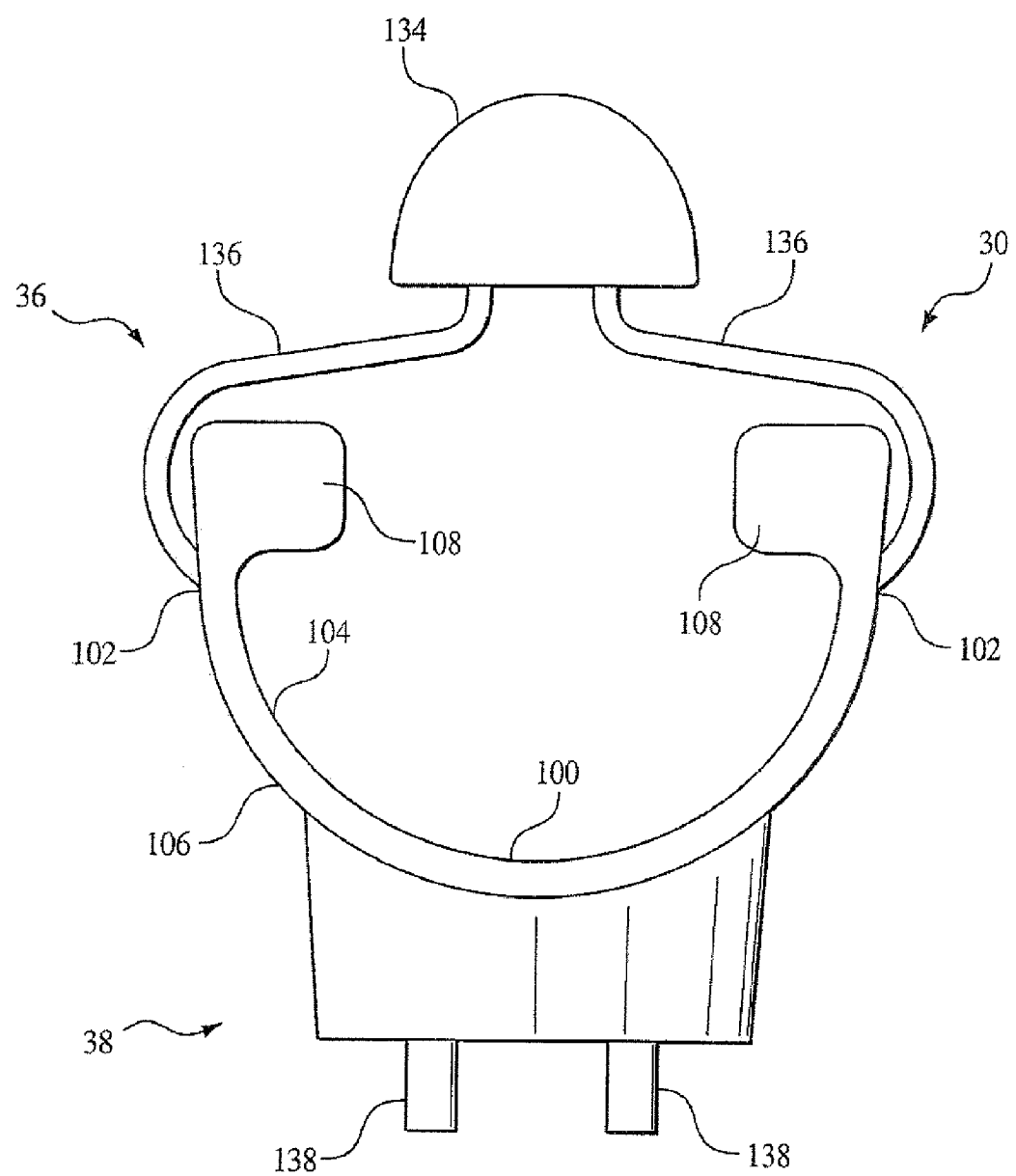
FIG. 18a is a top plan view of a sixth alternative embodiment.
Figure 18B:
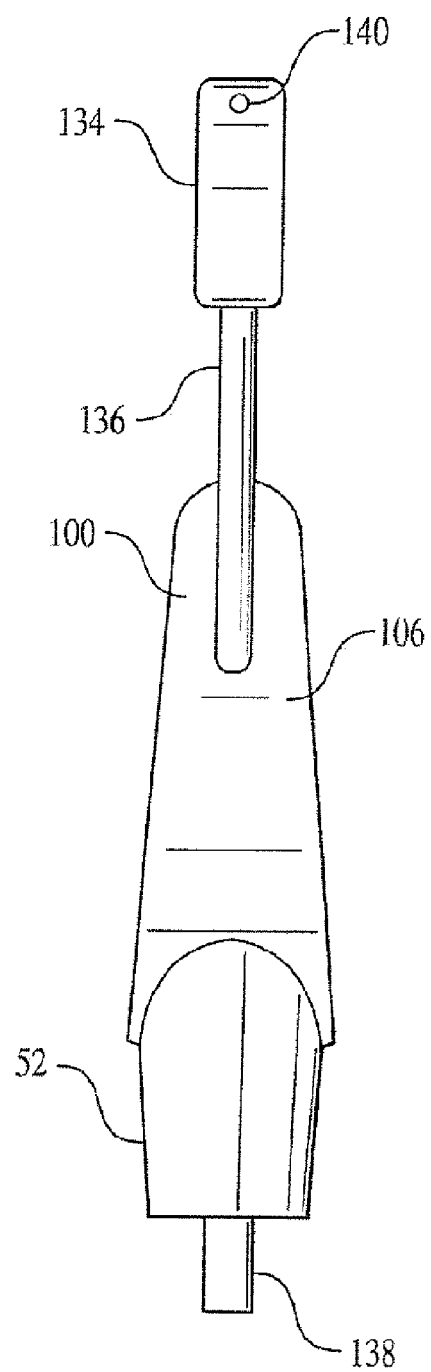
Figure 19A:
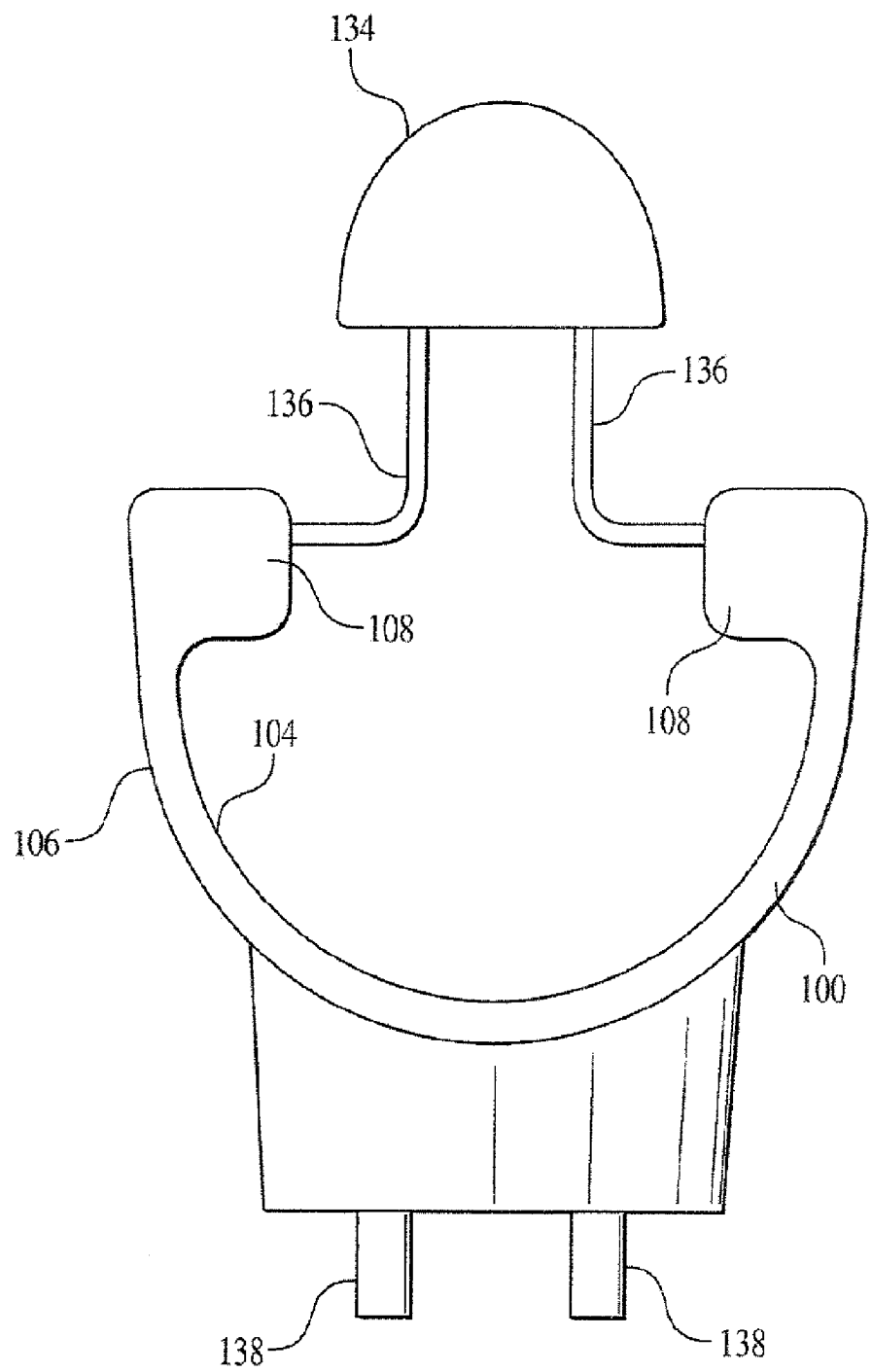
FIG. 19a is a top plan view of a seventh alternative embodiment.
Figure 19B:
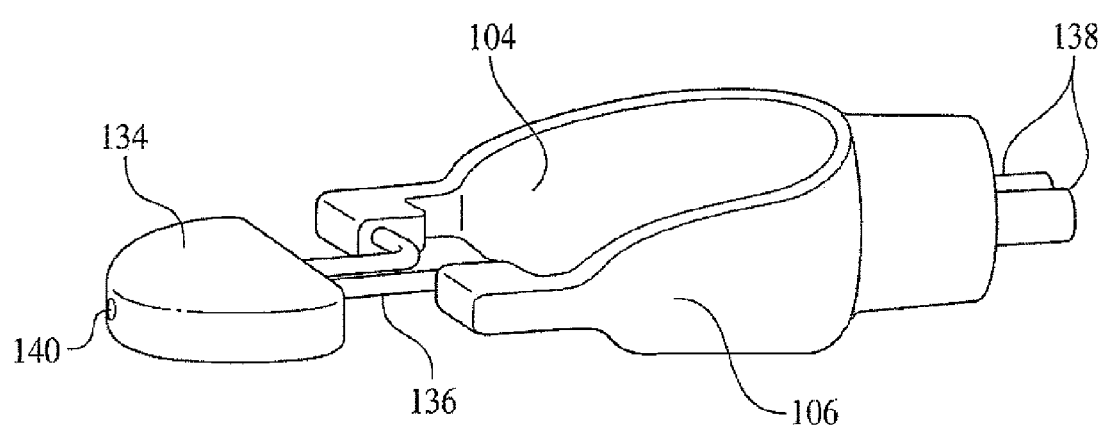

As seen in FIGS. 18a-19b, the inventors of the present invention contemplate the desirability of providing a mechanism to permit the user to breathe through their mouth without undermining the negative pressure environment within the user's oral cavity. In the prior embodiments disclosed herein, maintaining a negative pressure environment within the oral cavity requires the user to breathe through their nose. In the present alternative embodiment, the oral appliance includes a plug 134 sized and shaped to fit within the rear portion of the user's mouth in order to seal the oral cavity. Plug 134 includes posterior holes 140 that are in communication with tubes 136. The tubes, in turn, are connected to outlets 138 which are vented to the external environment. The tubes may be routed to the outer surface 106, as shown in FIG. 18a. Or, the tubes may extend from projections 108, as shown in FIG. 19a. In addition, the inventors further contemplate that the tubes may extend from a variety of other locations about the oral appliance such as from the inner surface 104.

The tubes are uniquely configured to provide a spring-like resiliency. When the oral appliance is fitted within the user's mouth, the tubes act like springs to bias the plug against the rear portion of the user's mouth. By so doing, the plug functions to provide a substantially hermetic seal, and, thus, maintain the negative pressure environment within the user's mouth. The tubes permit communication between the posterior holes 140 and the outlets 138 so that the user may breathe through these tubes without undermining the negative pressure environment in the user's mouth.

The tubes and the plug may be separate members attached together. In this configuration, the plug would be attached to the tubes and the tubes, in turn, would be attached to the first portion, or the second portion, of the oral appliance through a variety of known techniques such as mechanical adhesion, ultrasonic welding, thermal staking, and the like. In the presently preferred embodiment, the inventors contemplate forming the tubes integrally with the oral device. The internal lumen of the tubes, not shown, may be formed along with the oral appliance by using a lost-core molding process. In lost-core molding, the device is molded about an investment or lost core. Once the device has sufficiently hardened, the lost core is removed. In the present invention, the inventors contemplate dissolving the cores once the mold has sufficiently cured. Although a variety of materials could be used without departing from the scope of the present invention, the inventors contemplate that one such suitable material is Polyvinyl Alcohol. Polyvinyl Alcohol may be used as a lost core and then dissolved in water.

In use, the user would place oral appliance 30 of the present invention within their mouth such that the inner peripheral ridge 40 is just inside the user's teeth and outer peripheral ridge 42 is just outside the user's teeth thus capturing the user's teeth in first channel 44 and second channel 46. Once negative pressure supply 32 is activated, a subatmospheric pressure environment is created within the user's oral cavity. Alternatively, with respect to the embodiments shown in FIGS. 11-19b, the oral appliance is inserted such that outer peripheral ridge 42 is fitted between the user's teeth and gums thereby permitting the free movement of the user's tongue. Uniquely, this negative pressure environment is created within the user's mouth with minimal suctioning of the soft tissue inwardly due to the barrier provided by the outer peripheral ridge 42 and the unique location of apertures 48 adjacent the user's teeth. In addition, openings 114 can be located on the oral device proximate soft tissue to suction the soft tissue and assist in retaining the device in place. Further, the oral appliance may include plug 134 with tubes 136 to permit mouth breathing while maintaining a negative pressure oral environment.

Although the oral appliance of the present invention is shown with both the first channel and the second channel to accept both the upper and lower teeth of the user, the present invention could also be configured with only a single channel for only the upper or lower set of teeth. Similarly, the oral device may include a member that is configured to engage only the upper or lower set of teeth. Further, first portion 36 could be configured with a deformable material that may be applied to the region around either the first channel or the second channel so that the user can easily open their mouth while the oral appliance is in position.

Even though particular materials and methods of manufacture have been disclosed for the purposes of full disclosure, it should also be understood that the present invention is not intended to be limited to a particular material for the first portion or the second portion or a particular method of manufacture. Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims.

What is claimed is:

1. An oral appliance adapted to be connected to a negative pressure supply, the oral appliance comprising:
    a first portion having a first channel and a second channel, the first portion further including a plurality of apertures in the first channel and a plurality of apertures in the second channel, the first portion further including an internal cavity in communication with the plurality of apertures in the first channel and the plurality of apertures in the second channel;
    a second portion having an internal lumen in communication with the internal cavity; and
    a third portion fitted in the first channel.

2. The oral appliance as recited in claim 1, wherein the first portion is constructed from a flexible material and wherein the second portion is constructed from a rigid material.

3. The oral appliance as recited in claim 2, wherein the first portion is constructed of silicone molding compound.

4. The oral appliance as recited in claim 2, wherein the second portion is constructed of Polycarbonate.

5. The oral appliance as recited in claim 1, wherein the third portion is constructed of Ethylene-Vinyl-Acetate.

6. The oral appliance as recited in claim 1, wherein the first channel and second channel are offset relative to one another.

7. The oral appliance as recited in claim 1, wherein the first channel and second channel are aligned relative to one another.

8. The oral appliance as recited in claim 1, wherein the first channel and the second channel are configured to receive at least a portion of a user's teeth.

9. The oral appliance as recited in claim 8, wherein the plurality of apertures is located proximate to such a user's teeth or gums responsive to the oral appliance being disposed within such a user's mouth.

10. An assembly for providing negative pressure to a user's oral cavity, the assembly comprising:
    a negative pressure device; and
    an oral appliance including at least one aperture and further including an internal cavity in communication with the aperture and the negative pressure device, the oral appliance configured to be positioned on the periphery of the user's oral cavity without substantially extending into the user's oral cavity.

11. An oral appliance adapted to be connected to a negative pressure supply, the oral appliance comprising:
    a first portion having a first channel and a second channel, the first and second channels each configured to receive at least a portion of a user's teeth, the first portion further including a plurality of apertures in the first and second channels, the plurality of apertures located proximate to such a user's teeth or gums responsive to the oral appliance being disposed within such a user's mouth, the first portion further including an internal cavity in communication with the plurality of apertures; and
    a second portion having an internal lumen in communication with the internal cavity.

12. An assembly comprising:
    an oral appliance having a first portion having a first channel and a second channel, the first and second channels each configured to receive at least a portion of a user's teeth, the first portion further including a plurality of apertures in the first and second channels, the plurality of apertures located proximate to such a user's teeth or gums responsive to the oral appliance being disposed within such a user's mouth, the first portion further including an internal cavity in communication with the plurality of apertures, the oral appliance further including a second portion having an internal lumen in communication with the internal cavity;
    a negative pressure device; and
    a conduit interconnected between the negative pressure device and the oral appliance.

13. An oral appliance adapted to be connected to a negative pressure supply, the oral appliance comprising:
    a first portion having at least one channel that is configured to receive at least a portion of a user's teeth, the first portion further including a plurality of apertures in the at least one channel, the plurality of apertures located proximate to, and distributed over a substantial portion of, a user's teeth responsive to the oral appliance being disposed within a user's mouth, the first portion further including an internal cavity in communication with the plurality of apertures; and a second portion having an internal lumen in communication with the internal cavity.

14. An oral appliance adapted to be connected to a negative pressure supply, the oral appliance comprising:

a first portion having at least one channel that is configured to receive at least a portion of a user's teeth, the first portion further including at least one aperture in the at least one channel, the at least one aperture located proximate to rigid tissue of a user responsive to the oral appliance being disposed within a user's mouth, the first portion further including an internal cavity in communication with the at least one aperture;

a second portion having an internal lumen in communication with the internal cavity; and wherein at least one of the first and second portions includes an aperture located proximate to soft tissue of a user responsive to the oral appliance being disposed within a user's mouth.

15. An oral appliance adapted to be connected to a negative pressure supply, the oral appliance comprising:

a first portion having a first channel and a second channel, the first channel and the second channel each configured to receive at least a portion of a user's teeth, the first channel and the second channel being offset relative to one another, the first portion further including a first aperture in the first channel and a second aperture in the second channel, the first aperture and the second aperture each located proximate to a user's teeth or gums responsive to the oral appliance being disposed within a user's mouth, the first portion further including an internal cavity in communication with the first aperture and the second aperture; and a second portion having an internal lumen in communication with the internal cavity.

16. An oral appliance adapted to be connected to a negative pressure supply, the oral appliance comprising:

a first portion having at least one channel configured to receive at least a portion of a user's teeth, the first portion further including at least one aperture in the at least one channel, the at least one aperture located proximate to the posterior portion of a user's teeth or gums responsive to the oral appliance being disposed within a user's mouth, the first portion further including an internal cavity in communication with the at least one aperture; and a second portion having an internal lumen in communication with the internal cavity.

17. An oral appliance adapted to be connected to a negative pressure supply, the oral appliance comprising:

a first portion having a first channel and a second channel, the first channel and the second channel each configured to receive at least a portion of a user's teeth, the first channel and the second channel being offset relative to one another, the first portion further including at least one aperture in the first channel or the second channel, the at least one aperture located proximate to a user's teeth or gums responsive to the oral appliance being disposed within a user's mouth, the first portion further including an internal cavity in communication with the at least one aperture; and a second portion having an internal lumen in communication with the internal cavity.

* * * * *